United States Patent [19]
Jyouno et al.

[11] Patent Number: 5,707,504
[45] Date of Patent: Jan. 13, 1998

[54] OXYGEN CONCENTRATION DETECTOR

[75] Inventors: Kouji Jyouno; Isao Watanabe, both of Kariya, Japan

[73] Assignee: Nippondenso Co., Ltd., Japan

[21] Appl. No.: 588,327

[22] Filed: Jan. 18, 1996

[30] Foreign Application Priority Data

Jan. 19, 1995 [JP] Japan ................................. 7-026070
Nov. 28, 1995 [JP] Japan ................................. 7-334008

[51] Int. Cl.$^6$ ............................................. G01N 27/26
[52] U.S. Cl. ................................. 204/428; 204/424
[58] Field of Search ........................... 204/428, 429, 204/424

[56] References Cited

U.S. PATENT DOCUMENTS

| 4,019,974 | 4/1977 | Weyl et al. | 204/428 |
| 4,219,359 | 8/1980 | Miwa et al. | 204/428 |
| 5,238,552 | 8/1993 | Kato et al. | 204/428 |

FOREIGN PATENT DOCUMENTS

| 64-15956 | 1/1989 | Japan. |
| A-3-57949 | 3/1991 | Japan. |
| A-5-26842 | 2/1993 | Japan. |
| A-5-249069 | 9/1993 | Japan. |

Primary Examiner—Bruce F. Bell
Attorney, Agent, or Firm—Cushman Darby & Cushman, Intellectual Property Group of Pillsbury Madison & Sutro, LLP

[57] ABSTRACT

An oxygen concentration detector comprises a housing 10, a detecting element 12 with a built-in heater, a holder 2 made of an insulating ceramic and interposed between the housing and the detecting element 12, and a protecting cover 16 fixed to the housing 10 in such a manner as to cover the outside of the detecting element 12. The protecting cover 16 has gas inlets 160, and a protecting cylinder 21 formed by extending the holder 2 is interposed between the detecting element 12 and the protecting cover 16.

16 Claims, 18 Drawing Sheets

OXYGEN CONCENTRATION DETECTOR

BACKGROUND OF THE INVENTION

1. Field of the Invention

This invention relates to an oxygen concentration detector for use in an air-fuel ratio control in an internal combustion engine such as an automobile engine.

2. Description of the Related Art

Conventionally, an oxygen concentration detector having the following construction, for use in an air-fuel ratio control of an automobile engine, is known.

This oxygen concentration detector comprises a housing, a detecting element with a built-in heater, a holder made of an insulating ceramic and interposed between the housing and the detecting element and a protecting cover fixed to the housing in such a manner as to cover the outside of the detecting element, wherein the protecting cover has gas inlet ports.

In order for the detecting element to detect the oxygen concentration, the element must be at or above an element activation temperature. Therefore, when the temperature of a gas to be measured is low, immediately after the starting of an engine, and the detecting element cannot be heated by the gas to be measured, the oxygen concentration detector heats the detecting element, using its heater, so as to heat the detecting element to the element activation temperature.

In the oxygen concentration detector described above, moisture often enters from the gas inlet ports of the protecting cover during the use of the detector. When the temperature of the gas to be measured is sufficiently high, the moisture is evaporated and no problem develops.

When the temperature of the gas to be measured is low as described above, however, the moisture adheres to the detecting element without being evaporated. On the other hand, the detecting element is heated by the heater and attains a high temperature. Therefore, the adhering moisture imparts a thermal shock and cracks occur in the detecting element due to wetting.

To avoid this problem, some oxygen concentration detectors according to the prior art employ a double structure for the protecting cover and form a labyrinth structure so that moisture does not enter inside the protecting cover to the detecting element and the detecting element is difficult to be wetted.

However, the oxygen concentration detector described above uses a double protecting cover, and the number of components increases. The method of fixing the double protecting cover and its arrangement are difficult, and a great deal of trouble occurs in the production and assembly. For these reasons, the production cost of the oxygen concentration detector described above is high.

In view of these problems, the present invention aims at providing an oxygen concentration detector wherein cracks in a detecting element due to wetting do not easily occur and which is easy to assemble.

SUMMARY OF THE INVENTION

The invention provides an oxygen concentration detector comprising a housing, a detecting element with a built-in heater, a holder made of an insulating ceramic and interposed between the housing and the detecting element and a protecting cover so fixed to the housing as to cover the outside of the detecting element, wherein the protecting cover has gas inlet ports, and wherein a protecting cylinder formed by extending the holder is disposed between the detecting element and the protecting cover.

Next, the function and effect of the present invention will be explained.

The oxygen concentration detector according to the present invention includes the protecting cylinder extended between the detecting element and the protecting cover.

The moisture entering a chamber for a gas to be measured from the gas inlet ports of the projecting cover is cut off by the protecting cylinder and cannot reach the detecting element. Accordingly, cracking of the detecting element due to wetting hardly occurs. The housing is made of a heat-resistant metal such as a stainless steel.

The oxygen concentration detector according to the present invention employs a single protecting cover and yet has a wetting prevention function equivalent to that of a double protecting cover. The protecting cylinder is formed by extending the lower end portion of the holder. Therefore, the number of constituent components of the oxygen concentration detector can be reduced, and works such as welding, caulking, etc., of each component can be reduced to the extend corresponding to the decrease of the number of components.

Therefore, the oxygen concentration detector according to the present invention is easy to assemble.

The holder and the protecting cylinder are made of an insulating ceramic.

Accordingly, heat transfer of from the detecting element to the metallic housing through the holder can be prevented, and the heat-retaining property of the detecting element can be improved. In a limited current type detecting element whose output characteristics are likely to be affected by the temperature, therefore, the output characteristics are stabilized.

Further, the holder and the protecting cylinder can electrically insulate the detecting element. Therefore, leakage of the output current of the detecting element to the metallic housing can be prevented, and the output characteristics of the detecting element can be further stabilized.

The insulating ceramic is preferably a ceramic which is different from the ceramic constituting the detecting element, has high hardness and is dense and gas-impermeable. Examples of such ceramics are alumina ceramics, silicon nitride ceramics, and so forth.

Besides a laminate type detecting element described in the later-appearing Embodiment 1, a cup type detecting element can be used as the detecting element described above.

Next, the lower end of the protecting cylinder is preferably open.

To correctly detect the oxygen concentration, the detecting element must keep sufficient contact with the gas to be measured. According to the construction described above, the gas to be measured can easily flow into the inside of the protecting cylinder from the open lower end. Therefore, deposition of the moisture to the detecting element can be prevented without impeding oxygen concentration detection.

Because the lower end is open, the protecting cylinder can be easily produced.

Next, the protecting cylinder preferably has openings through which the gas to be measured flows, and the openings are disposed in such a manner as not to oppose the gas inlet ports of the protecting cover.

According to this construction, a labyrinth structure is defined between the protecting cover and the protecting cylinder and this labyrinth structure can prevent the moisture entering through the gas inlet ports from reaching the detecting element through the opening.

Next, the protecting cylinder preferably has a bottom plate.

Therefore, a wide area, from the side surface of the detecting element to its bottom surface, can be protected from the moisture.

The bottom plate of the protecting cylinder preferably has an opening.

According to this construction, the gas to be measured can easily flow into the protecting cylinder from the opening at the bottom plate but the moisture cannot flow easily. Therefore, deposition of the moisture to the detecting element can be prevented without impeding oxygen concentration detection.

Next, the bottom plate of the protecting cylinder protrudes from the cover bottom plate of the protecting cover, and an opening is preferably disposed between the protecting cylinder and the cover bottom plate.

The moisture entering the chamber from the gas inlet ports can be discharged from this opening.

When the oxygen concentration detector is disposed inside the flow of the gas to be measured, the protecting cylinder opens at the bottom plate thereof to the flow of the gas. Therefore, a flow of gas flowing from the opening of the bottom plate of the protecting cylinder to the outside of the oxygen concentration detector occurs, and the quantity of the gas flowing into and out from the protecting cylinder can be increased. This means that response of the oxygen concentration detector can be further improved.

Next, the protecting cylinder preferably has an opening, into which the gas to be measured flows, above the open end of the housing.

This opening is so disposed as to oppose the inner surface of the housing. Therefore, moisture cannot easily enter from this opening.

Further, the opening is disposed in the vicinity of the upper portion of the detecting element, and is therefore spaced apart from the distal end of the detecting element which attains the highest temperature. Therefore, even when the moisture enters from the opening and wets the detecting element, the wetted portion is the portion at which the temperature is low. Accordingly, the thermal impact due to wetting is smaller than when the distal end is wetted, and the occurrence of cracks can be reduced.

Next, the bottom plate of the protecting cylinder preferably has a thick protruding portion smaller than the outer diameter of the bottom plate, the thick protruding portion has an opening, the lower end surface of this thick protruding portion exists on the same plane as the cover bottom plate or protrudes from the cover bottom plate, and an opening is preferably disposed between the thick protruding portion and the cover bottom plate.

The moisture entering the chamber for a gas to be measured from the gas inlets of the protecting cover can be discharged from the opening.

When the oxygen concentration detector described above is disposed inside the flow of the gas to be measured, the protecting cylinder is open, at the bottom plate thereof, to the gas flow. Therefore, a flow of the gas flowing from the opening formed in the thick protruding portion of the protecting cylinder to the outside of the oxygen concentration occurs, and the gas to be measured can flow more easily into the protecting cylinder.

Next, the bottom plate of the protecting cylinder is preferably positioned more inward than the cover bottom plate of the protecting cover. It is further preferred that an opening is formed in the bottom plate of the protecting cylinder, and an opening is also formed in the cover bottom plate of the protecting cover.

It is also preferred that the lower end of the protecting cylinder is open, and the cover bottom plate of the protecting cover has an opening.

According to this construction, the gas to be measured can easily flow into the protecting cylinder from the open lower end or from the opening of the bottom plate. Therefore, deposition of the moisture to the detecting element can be prevented without impeding oxygen concentration detection.

Further, the moisture entering the chamber for a gas to be measured from the gas inlet ports can be discharged from the opening.

When the oxygen concentration detector is disposed in the flow of the gas to be measured, the chamber for a gas to be measured is open at the cover bottom plate thereof to the flow of gas to be measured, and the protecting cylinder is open at the bottom plate thereof to the chamber for a gas to be measured. Therefore, the flow of the gas flowing from the opening of the bottom plate of the protecting cylinder to the outside of the oxygen concentration detector occurs, and the gas to be measured can flow more easily into the protecting cylinder.

Next, the lower end of the protecting cylinder is an open end, the cover bottom plate of the protecting cover has an opening, and this opening is preferably bent at the end thereof in such a manner as to face the open lower end of the protecting cylinder.

According to this construction, the moisture entering the chamber for a gas to be measured from the gas inlet ports can be discharged from this opening.

Further, because the open lower end is bent, the clearance defined between the lower end of the protecting cylinder and the bent open end of the opening can be reduced. Accordingly, the moisture flowing from the gas inlet ports can be entrapped within the protecting cylinder, and deposition of the moisture to the detecting element can be prevented.

Further, the present invention preferably provides the oxygen concentration detector wherein the detecting element described above comprises a sheet-like solid electrolyte; a gas-to-be-measured side electrode disposed on a first surface of the sheet-like solid electrolyte; a reference gas side electrode disposed on a second surface opposite to the first surface of the sheet-like solid electrolyte; a sheet-like insulator laminated with the sheet-like solid electrolyte; the sheet-like insulator forming a space as a reference gas chamber between the sheet-like solid electrolyte and the sheet-like insulator; the space being closed at a first end portion thereof on the side of the detection side and being open at a second end portion thereof; and a heater formed on the sheet-like insulator on the opposite side to the sheet-like solid electrolyte.

The detecting element of the oxygen concentration detector described above has a flange portion between the first and second ends thereof, and the holder holds the detecting element at the flange portion.

In addition to the above construction, the detecting element may have a structure comprising a solid electrolyte having a shape of a cylinder with a closed end, a gas-to-bemeasured side electrode on an outer surface of the cylinder, a reference gas side electrode on an inner surface of the cylinder, and a heater inside the cylinder (see FIG. 29).

The substantially the same effect as above can be obtained by making the extended portion from the housing instead of the holder, and this extended portion of the housing can have the same various features as those mentioned for the extended portion of the holder before and after. For example, the extended portion has an opening at the end thereof.

Besides a linear air-fuel ratio sensor of automobile engines, the oxygen concentration detector according to the present invention can be used as a stoichiometric sensor, that is, a sensor for detecting a stoichiometric air-fuel ratio.

DESCRIPTION OF THE PREFERRED EMBODIMENTS

Embodiment 1

An oxygen concentration detector according to Embodiment 1 of the present invention will be explained with reference to FIGS. 1 to 4.

By the way, the oxygen concentration detector of this embodiment is disposed in an exhaust passage so as to control the air-fuel ratio of an automobile engine.

Figure 1:
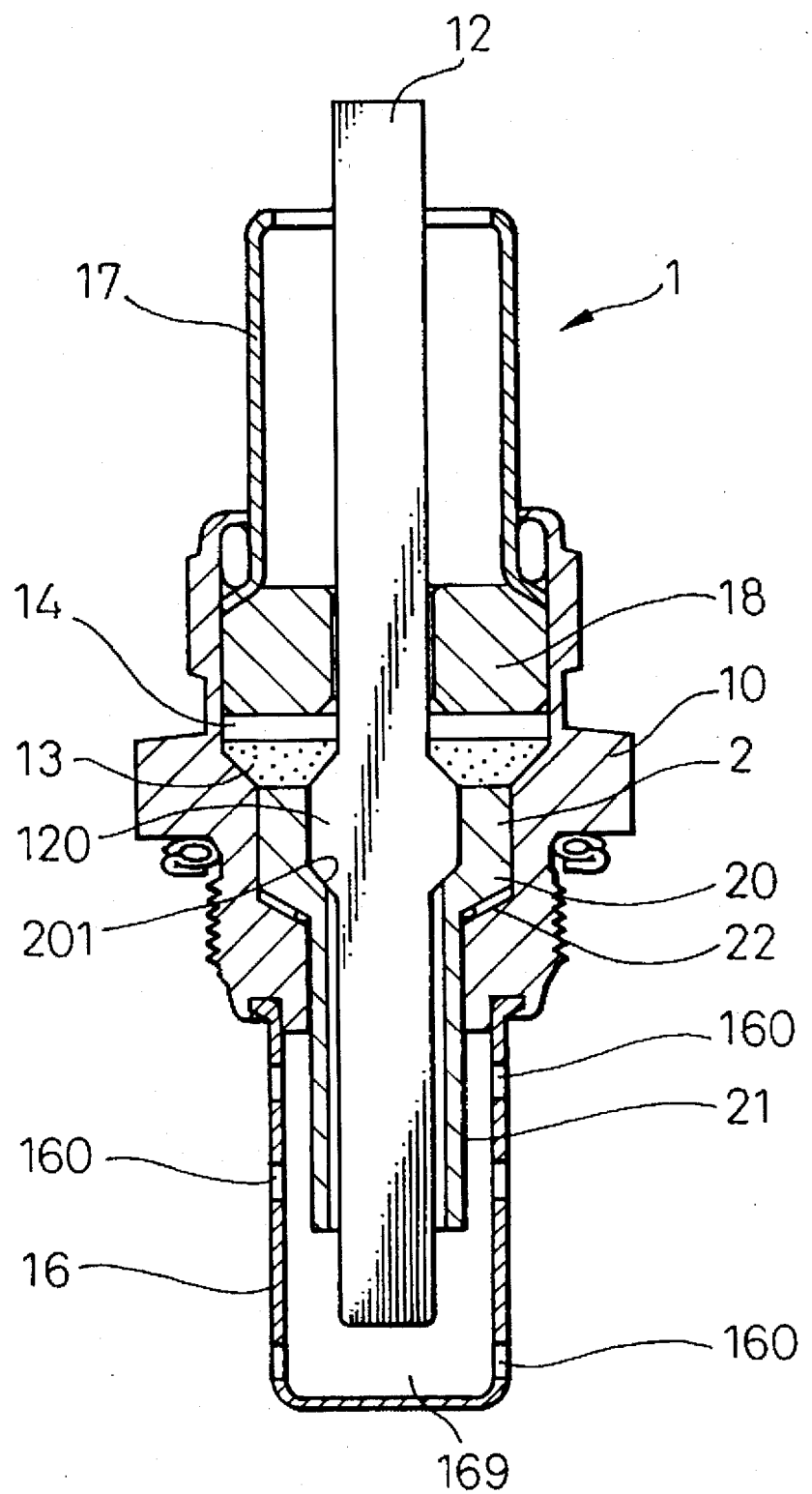
FIG. 1 is a sectional explanatory view of principal portions of an oxygen concentration detector according to Embodiment 1 of the present invention.

As shown in FIG. 1, the oxygen concentration detector 1 of this embodiment comprises a housing 10, a detecting element 12 with a built-in heater 45 (FIG. 3), a holder 2 made of an insulating ceramic and sandwiched between the housing 10 and the detecting element 12, and a protecting cover 16 so fixed to the housing 10 as to cover the outside of the detecting element 12, and the protecting cover 16 has a plurality of gas inlet ports 160.

A protecting cylinder 21 formed by extending the holder 2 described above is interposed between the detecting element 12 and the protecting cover 16.

Figure 2:
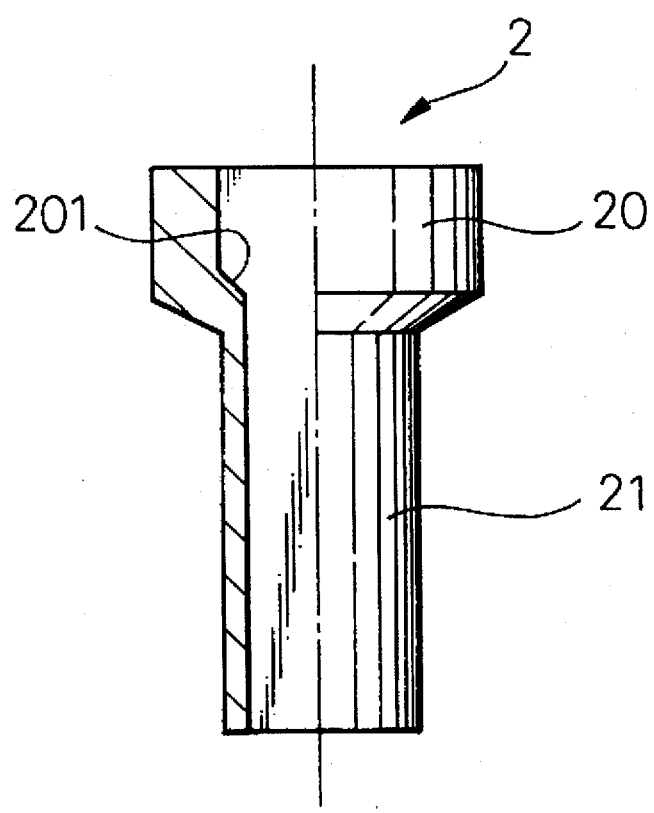
FIG. 2 is an explanatory view showing a holder in Embodiment 1.

The holder 2 is made of a hard, dense and gas-impermeable alumina ceramic, and comprises a holding portion 20 having an inclined receiving surface 201 for holding the detecting element 12 and a protecting cylinder 21 disposed below this holding portion 20 (FIG. 2).

The lower end of the protecting cylinder 21 is open, and this cylinder 21 is disposed in such a manner as to shield the portion between the gas inlet ports 160 and the detecting element 12. The distal end of the protecting cylinder 21 exists above the lower end of the protecting cover and above the distal end of the detecting element 12.

The detecting element 12 is fixed inside the holder 2 by a powder member 13 which is pressed and packed by a pad 14 and a supporter 18 above its flange portion 120.

In FIG. 1, reference numeral 169 denotes a chamber for a gas to be measured, reference numeral 17 denotes a cover on the atmosphere side and reference numeral 22 denotes a packing washer.

Figure 3:
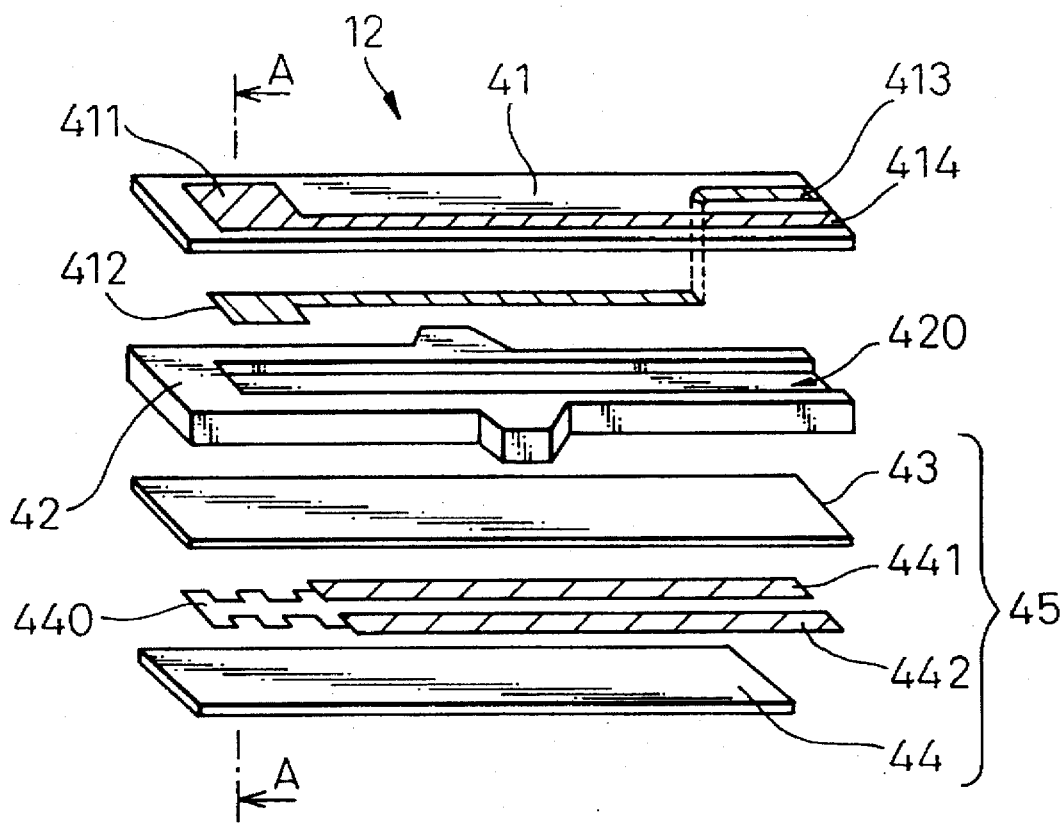
FIG. 3 is an exploded explanatory view of a detecting element in Embodiment 1.
Figure 4:
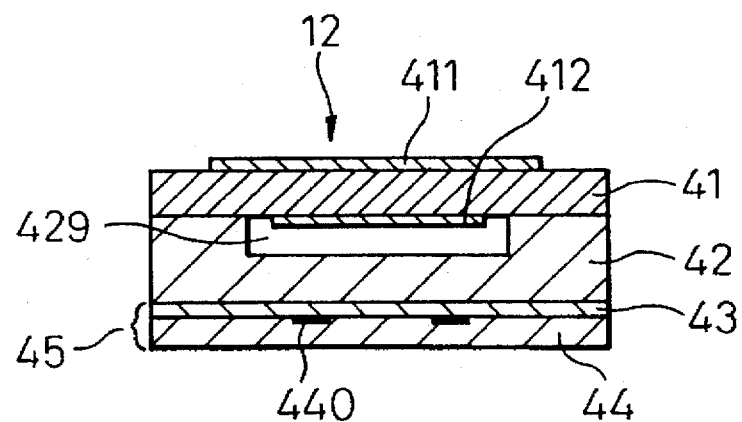
FIG. 4 is a sectional view of the detecting element in Embodiment 1.

As shown in FIGS. 3 and 4, the detecting element 12 described above is a laminate type detecting element 12 having a flange portion on the side surface thereof.

The detecting element 12 comprises a sheet-like solid electrolyte 41 and an alumina substrate 42 laminated with the solid electrolyte 41. The solid electrolyte 41 and a groove portion 420 formed in the alumina substrate 42 together define a reference gas chamber 429.

A gas-to-be-measured side electrode 411 is disposed on one of the surfaces of the solid electrolyte 41 and a reference gas side electrode 412 is disposed on the other. Lead portions 413 and 414 are provided to the gas-to-be-measured side electrode 411 and the reference gas side electrode 412, respectively, and the output of the detecting element 12 can be taken out through the lead portions 413, 414 (not shown in the drawing).

A heater portion 45 is disposed on the surface opposite to the surface on which the groove portion 420 is disposed. The heater portion 45 comprises a heat generation member 440 and lead portions 441, 442 that are bonded to the alumina substrate 43 by a tungsten paste, and an insulating cover 44 covering the upper portion of the heat generation member 440 and the lead portions 441, 442. By the way, the lead portions 441, 442 are connected to a current feed line to the heat generation member 440.

Figure 29:
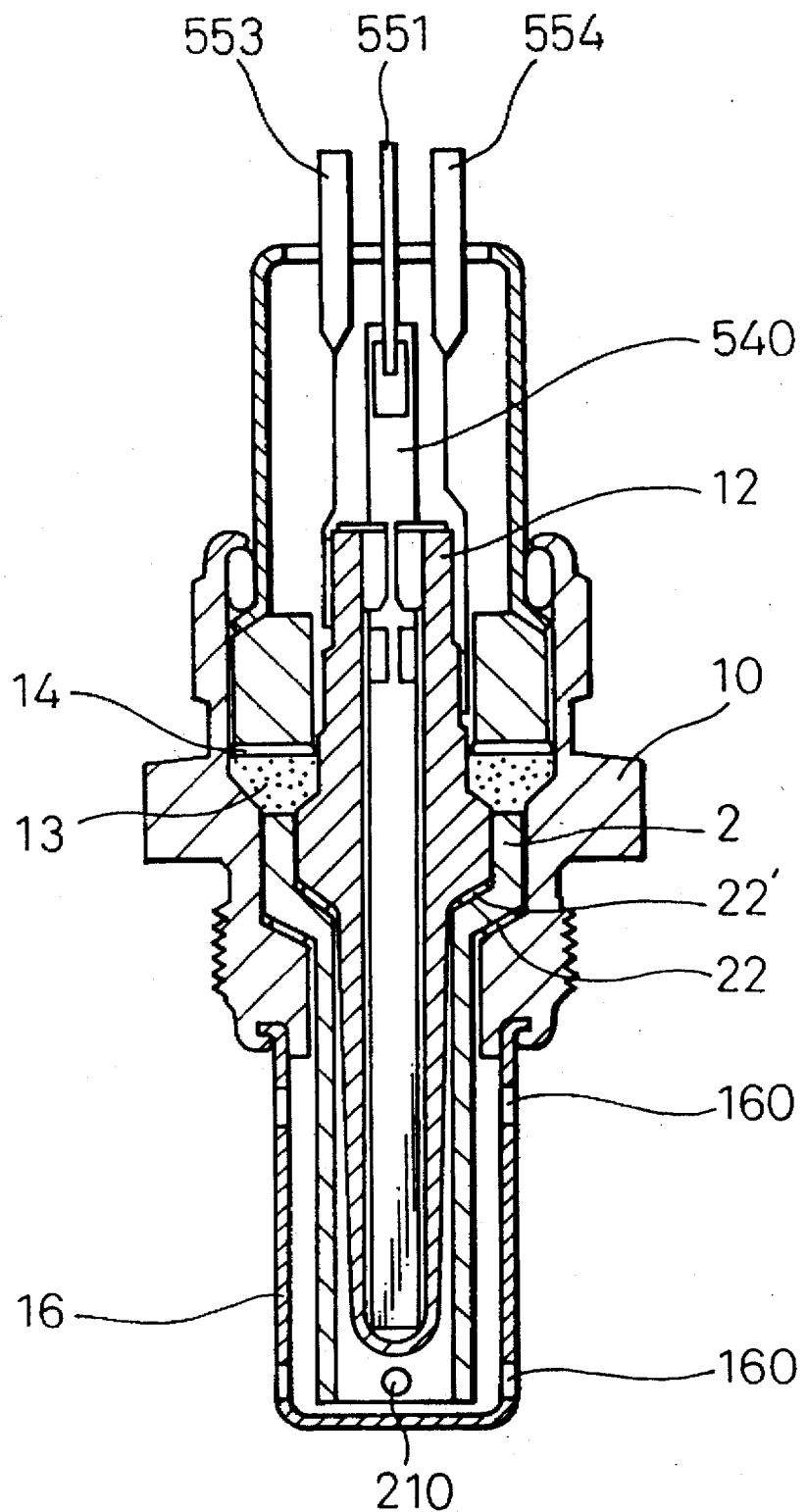
FIG. 29 is a sectional explainatory view of principal portions of an oxygen concentration detector using a cup-shaped oxygen concentration detecting element.

The construction of the detecting element is not limited to the construction described above. For example, it may have a known construction wherein a gas-to-be-measured side electrode is disposed on the outer surface of a cup-shaped solid electrolyte, a reference gas side electrode is disposed on the inner surface, and a heater is disposed inside the solid electrolyte (FIG. 29).

Next, the function and effect of this embodiment will be explained.

The oxygen concentration detector 1 of this embodiment includes a water-proofing protecting cylinder 21 disposed between the detecting element 12 and the protecting cover 16.

Therefore, the moisture entering the chamber for a gas to be measured 169 through the gas inlet ports 160 of the protecting cover 16 is cut off by the protecting cylinder 21 and does not easily reach the detecting element 12.

In the oxygen concentration detector 1 of tis embodiment, the protecting cover 16 need not have a double structure, and the protecting cylinder 21 is extended with respect to the holder. Therefore, the number of components can be reduced, and an oxygen concentration detector 1 which is easy to produce and whose components are easy to assemble can be obtained.

The oxygen concentration detector 1 of this embodiment has a water-proofing function of the detecting element 12 similar to the water-proofing function of a double protecting cover, by using a single protecting cover. Since the protecting cylinder 21 is formed by extending the lower end of the holder 2, the number of constituent components of the oxygen concentration detector 1 can be reduced. Fixing work of each component such as welding, caulking, etc., becomes easier to the extend corresponding to the reduction of the number of constituent components.

Accordingly, the oxygen concentration detector of this embodiment is easy to assemble.

The holder 2 and the protecting cylinder 21 are made of an insulating ceramic.

Therefore, the heat transfer from the detecting element 12 to the metallic housing 10 through the holder 2 can be prevented, and the heat-retaining property of the detecting element 12 can be improved. For this reason, the output characteristics of a limited current type detecting element 12, whose output characteristics are likely to be affected by temperature, can be particularly stabilized.

Further, the holder 2 and the protecting cylinder 21 can electrically insulate the detecting element 12. In other words, leakage of the output current of the detecting element 12 to the metallic housing 10 can be prevented, too, and the output characteristics of the detecting element 12 can be further stabilized.

The lower end of the holder 2 is open. Therefore, the holder 2 can be produced more easily.

Embodiment 2

Figure 5:
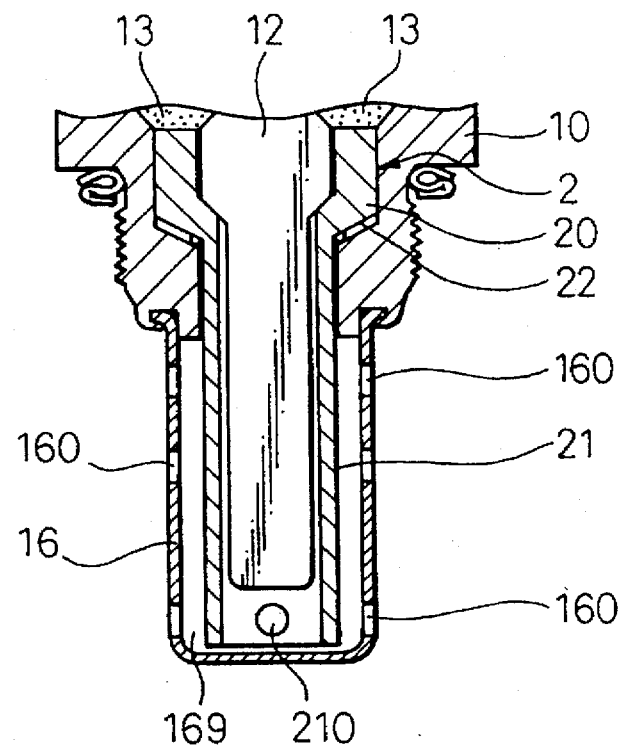
FIG. 5 is a sectional explanatory view of principal portions of an oxygen concentration detector wherein a protecting cylinder is extended to the lower end of a detecting element in Embodiment 2 according to the present invention.
Figure 6:
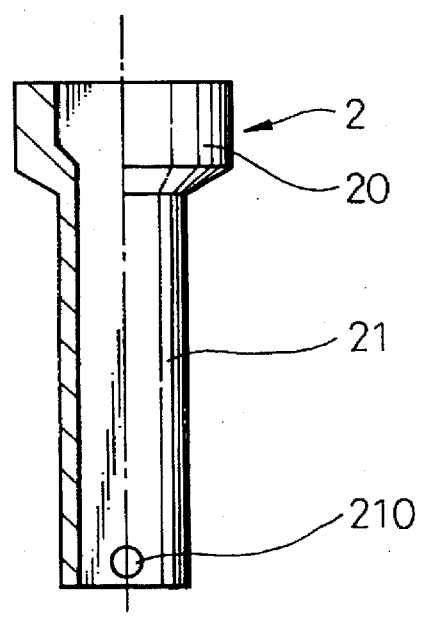
FIG. 6 is an explanatory view of a holder in Embodiment 2.

This embodiment provides an oxygen concentration detecting element 12 equipped with a protecting cylinder 21 which covers the full side surface of the detecting element 12 as shown in FIGS. 5 and 6.

An opening 210, through which a gas to be measured flows in, is formed on the distal end side surface of the protecting cylinder 21, and is so disposed as not to face the gas inlets 160 of the protecting cover 16.

The rest of the construction is the same as that of Embodiment 1.

In the oxygen concentration detector 1 of this embodiment, the full side surface of the detecting element 12 is covered with the protecting cylinder 21. Therefore, it becomes more difficult for moisture to deposition to the detecting element 12.

Because the protecting cylinder 21 has the opening 210, the gas to be measured can freely enter the protecting cylinder 21, so that the protecting cylinder 21 does not impede the oxygen concentration detection of the detecting element 12.

The opening 210 does not oppose the gas inlet port 160. Therefore, a labyrinth structure is defined between the protecting cover 16 and the protecting cylinder 21, and invasion of moisture into the protecting cylinder 21 can be effectively prevented.

Further, the powder member 13 is packed to the upper portion of the holder 2 so as to fix the detecting element 12. Because the protecting cylinder 21 is extended below the protecting cover 16, it becomes possible to prevent the gas to be measured having a high temperature from directly impinging against the powder member 13. Therefore, deterioration of the powder member 13 and the drop of air-tightness of the oxygen concentration detector resulting from this deterioration can be prevented.

This embodiment has the same function and effect as that of the first embodiment.

Embodiment 3

Figure 7:
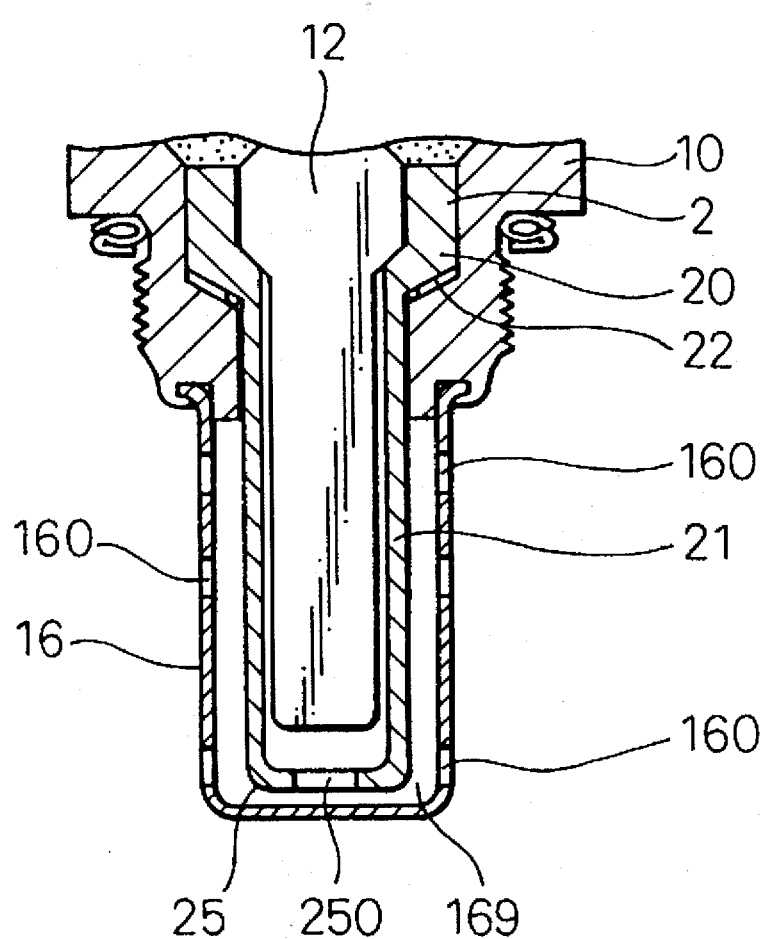
FIG. 7 is a sectional view of an oxygen concentration detector wherein a protecting cylinder has a bottom plate, in Embodiment 3, according to the present invention.
Figure 8:
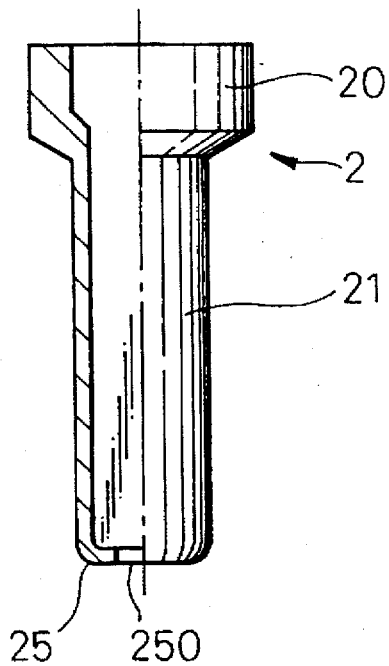
FIG. 8 is an explanatory view of a holder in Embodiment 3.
Figure 9:
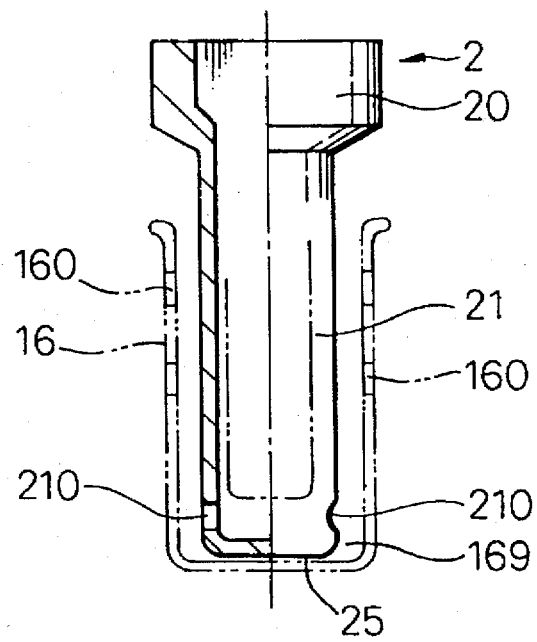
FIG. 9 is an explanatory view of the holder and the protecting cylinder in Embodiment 3.

This embodiment provides an oxygen concentration detector wherein a bottom plate 25 is provided to the protecting cylinder 21 as shown in FIGS. 7 to 9.

FIGS. 7 and 8 show an oxygen concentration detector wherein an opening 250 is formed in the bottom plate 25 of the protecting cylinder 21.

FIG. 9 shows an oxygen concentration detector wherein the opening 210 is disposed at the lower end side surface of the protecting cylinder 21 in such a manner as not to oppose the gas inlets 160 of the protecting cover 16.

The rest of the construction is the same as that of Embodiment 1.

In the oxygen concentration detector of this embodiment, the side surface and the bottom surface of the detecting element 12 are covered with the protecting cylinder 21 and its bottom plate 25. Further, because the openings 210 and 250 do not oppose the gas inlets 160, a labyrinth structure is defined between the protecting cover 16 and the protecting cylinder 21, and consequently, invasion of moisture into the protecting cylinder 21 can be prevented further effectively.

Because the protecting cylinder 21 has the openings 210 and 250, the gas to be measured can flow into the protecting cylinder 21. Accordingly, the protecting cylinder 21 does not impede the detection of the oxygen concentration by the detecting element 12.

This embodiment provides the same function and effect as that of Embodiment 1.

Embodiment 4

As shown in FIGS. 10 to 13, this embodiment has the construction wherein an opening 215 into which the gas to be measured flows is disposed above an open end 108 of the housing 10 in the protecting cylinder 21.

The opening 215 in the protecting cylinder 21 is disposed at the opposed surface portion between the holder 2 and the housing 10, and the open end 108 of the housing 10 is expanded outward in such a manner as to define a conduction route 109 of the gas to be measured with the holder 2.

Figure 10:
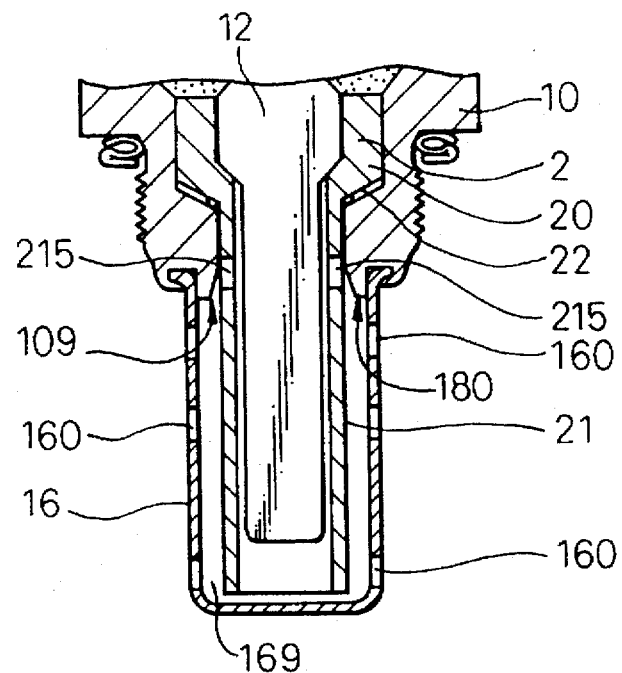
FIG. 10 is a sectional explanatory view of principal portions of an oxygen concentration detector having an opening at an upper part of a protecting cylinder in Embodiment 4 according to the present invention.

FIG. 10 shows an oxygen concentration detector wherein the lower end of the protecting cylinder 21 is open in the same way as in Embodiment 2.

Figure 11:
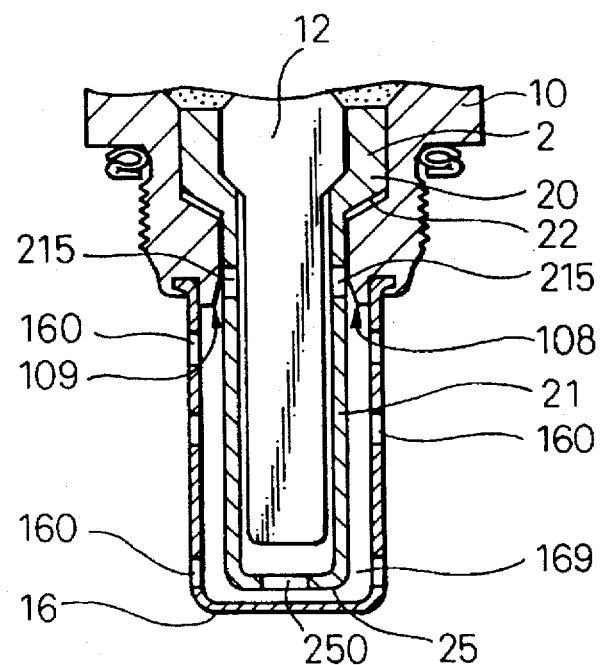
FIG. 11 is a sectional explanatory view of another oxygen concentration detector in Embodiment 4.

FIG. 11 shows an oxygen concentration detector wherein the protecting cylinder 21 has the bottom plate 25 in the same way as in Embodiment 3. The bottom plate 25 has an opening 250.

Figure 12:
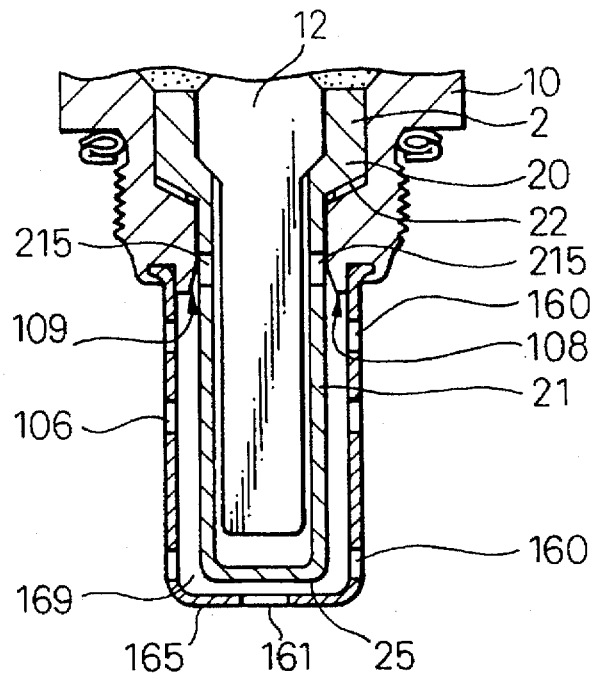
FIG. 12 is a sectional explanatory view of principal portions of still another oxygen concentration detector in Embodiment 4.

FIG. 12 shows an oxygen concentration detector wherein the side surface and the bottom surface of the detecting element 12 are completely covered with the protecting cylinder 21 and the lower end of the protecting cover 16 is open. In other words, an opening 161 is formed in the cover bottom plate 165 of the protecting cover 16.

Figure 13:
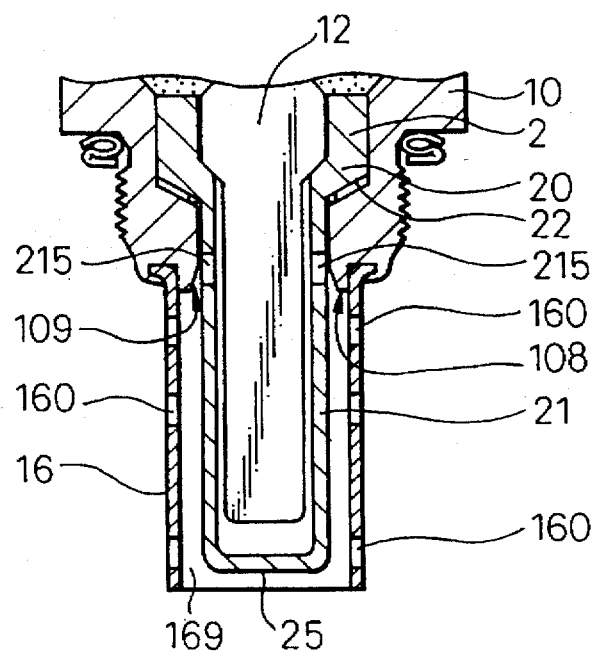
FIG. 13 is a sectional explanatory view of principal portions of still another oxygen concentration detector in Embodiment 4.

FIG. 13 shows an oxygen concentration detector wherein the lower end of the protecting cover 16 is open. In other words, the protecting cover 16 is not equipped with the cover bottom plate.

The rest of the construction is the same as that of Embodiment 1.

In each of the oxygen concentration detectors of this embodiment, the opening 215 is so disposed as to open to only the conduction route 109 defined between the holder 2 and the housing 10. Therefore, the moisture that enters the chamber 169 for a gas to be measured cannot easily pass through the opening 215.

The opening 215 is disposed in the proximity of the upper portion of the detecting element 12, and is therefore spaced apart from the distal end of the detecting element 12 which attains the highest temperature. Therefore, even when the moisture enters from the opening 215 and wets the detecting element 12, the wetted portion is the portion at which the temperature is low, so that the thermal impact due to wetting is smaller than when the distal end is wetted, and the occurrence of cracking can be restricted.

This embodiment provides the same function and effect as that of Embodiment 1.

By the way, the lower end of the protecting cover 16 is open in the oxygen concentration detector shown in FIG. 13. Therefore, this embodiment can prevent the moisture from staying between the protecting cover 16 and the bottom plate 25 of the protecting cylinder 21 and can discharge the moisture entering the chamber 169 for a gas to be measured.

Embodiment 5

Figure 14:
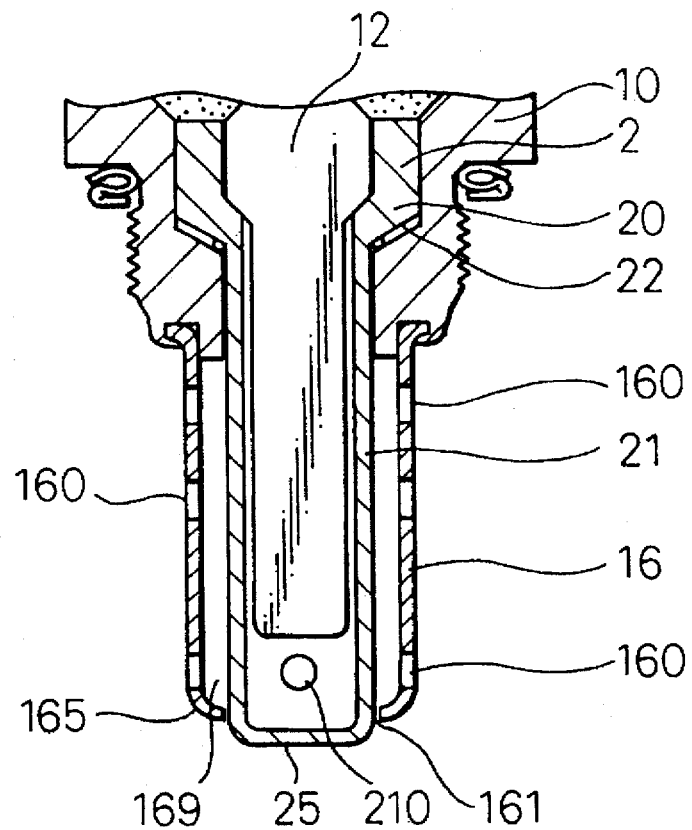
FIG. 14 is a sectional explanatory view of principal portions of an oxygen concentration detector equipped with a holder having a protruding bottom plate.
Figure 15:
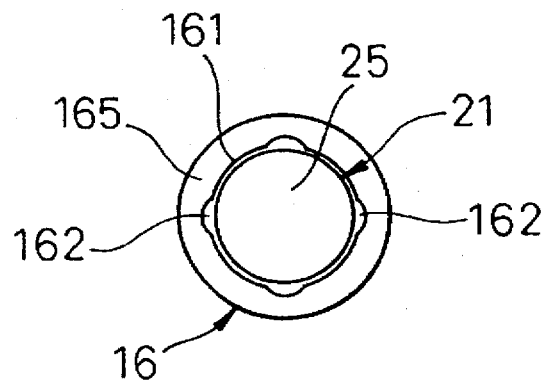
FIG. 15 is a bottom view of an oxygen concentration detector according to Embodiment 5 of the present invention.

As shown in FIGS. 14 and 15, this embodiment provides an oxygen concentration detector wherein the bottom plate 25 of the protecting cylinder 21 protrudes from the cover bottom plate 165 of the protecting cover 16, and an opening 161 is disposed between the protecting cylinder 21 and the cover bottom plate 165.

The opening 161 having a diameter greater than that of the protecting cylinder 21 is disposed in the cover bottom plate 165 of the protecting cover 16. Large diameter portions 162 are formed at four positions of the outer periphery of the opening 161.

The protecting cylinder 21 has a bottom plate 25 in the same way as in Embodiment 2, the opening 210 into which the gas to be measured flows is disposed at the distal end side surface of the protecting cylinder 21, and moreover, this opening 210 is so disposed as not to oppose the gas inlets 160 of the protecting cover 16.

The rest of the construction is the same as that of Embodiment 1.

The oxygen concentration detector of this embodiment includes the opening 161 having the large diameter portions 162 between the cover bottom plate 165 of the protecting cover 16 and the bottom plate 25 of the protecting cylinder 21. Therefore, this embodiment can prevent the moisture from staying between the protecting cover 16 and the protecting cylinder 21.

This embodiment has the same function and effect as that of Embodiment 1.

Embodiment 6

Figure 16:
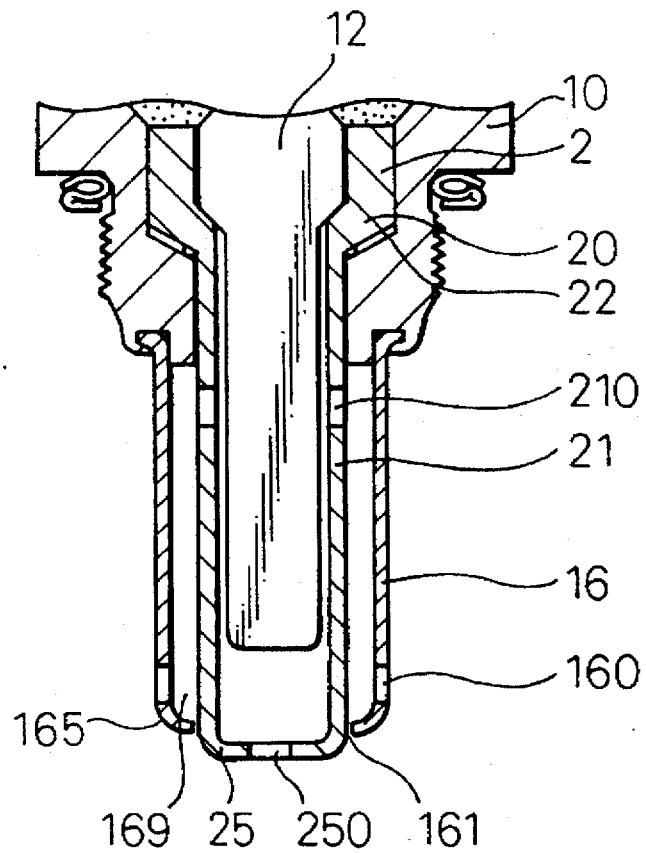
FIG. 16 is a sectional explanatory view of principal portions of an oxygen concentration detector equipped with a holder having a protruding bottom plate according to Embodiment 6 of the present invention.
Figure 17:
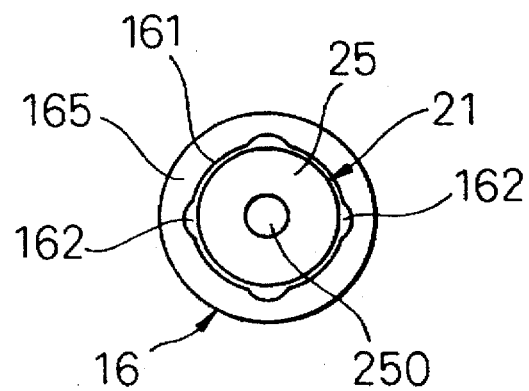
FIG. 17 is a bottom view of the oxygen concentration detector in Embodiment 6.
Figure 18:
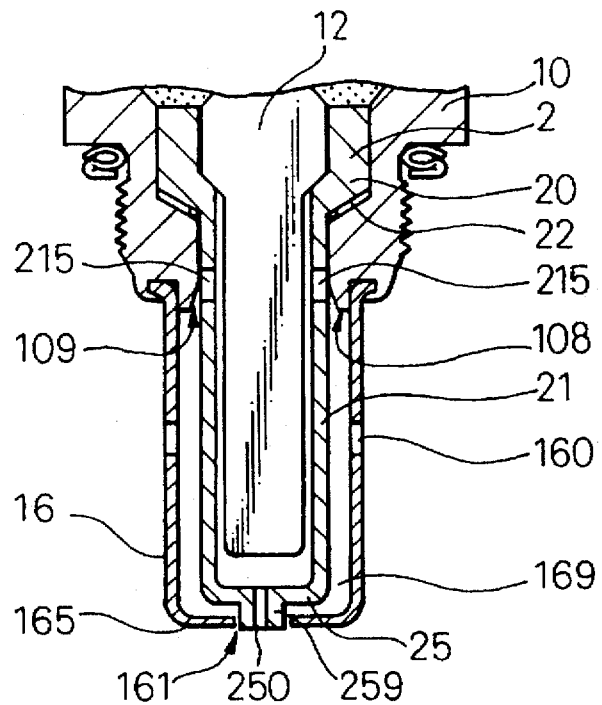
FIG. 18 is a sectional explanatory view of principal portions of an oxygen concentration detector equipped with a holder having a thick protruding portion on a bottom plate in Embodiment 7 according to the present invention.
Figure 19:
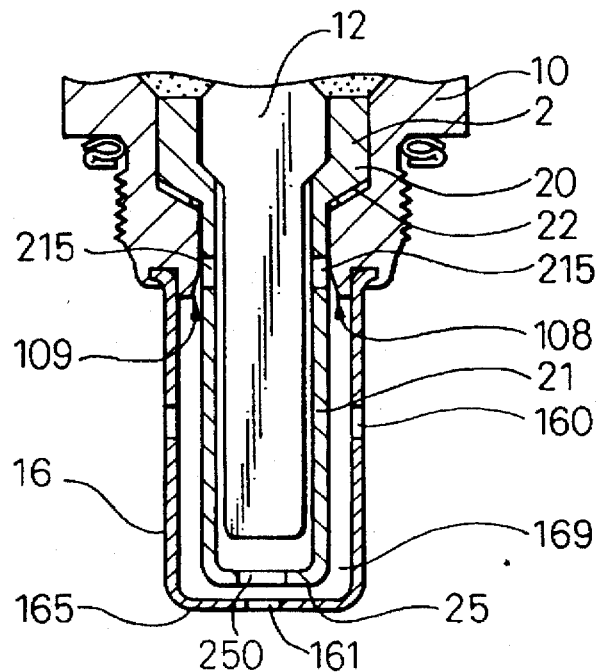
FIG. 19 is a sectional explanatory view of principal portions of an oxygen concentration detector wherein openings are formed on a bottom plate and a cover bottom plate, respectively, according to Embodiment 8 of the present invention.

As shown in FIGS. 16 and 17, this embodiment provides an oxygen concentration detector wherein the bottom plate 25 of the protecting cylinder 21 protrudes from the cover bottom plate 165 of the protecting cover 16, and the opening 161 is defined between the protecting cylinder 21 and the cover bottom plate 165. The large diameter portions 162 are formed at four positions of the outer periphery of the opening 161.

The protecting cylinder 21 has the bottom plate 25 in the same way as in Embodiment 2 and an opening 210 into which the gas to be measured flows is formed on the side of the protecting cylinder 21 in such a manner as not to oppose the gas inlets 160 of the protecting cover 16.

An opening 250 is also formed in the bottom plate 25 of the protecting cylinder 21.

The rest of the construction is the same as that of Embodiment 1.

In the oxygen concentration detector of this embodiment, the opening 161 having the large diameter portions 162 is disposed between the cover bottom plate 165 of the protecting cover 16 and the bottom plate 25 of the protecting cylinder 21. Therefore, this embodiment can prevent moisture from staying between the protecting cover 16 and the protecting cylinder 21, and can discharge the moisture entering the chamber for a gas to be measured 169.

The oxygen concentration detector described above is disposed in the flow of the gas to be measured. Since the bottom plate 25 of the protecting cylinder 21 protrudes from the cover bottom plate 165 of the protecting cover 16, the opening 250 opens to the gas flow.

Accordingly, a gas flow flowing from the opening 250 to the outside of the oxygen concentration detector develops and the quantity of the gas to be measured flowing into and out from the protecting cylinder 21 from this opening 210 can be increased. In consequence, the response of the oxygen concentration detector can be further improved.

The function and effect of this embodiment is the same as that of Embodiment 1.

Embodiment 7

This embodiment provides an oxygen concentration detector equipped with a thick protruding portion 259 disposed on the bottom plate 25 of the protecting cylinder 21.

The thick protruding portion 259 smaller than the outer diameter of the bottom plate 25 is disposed on the bottom plate 25 of the protecting cylinder 21. The lower end face of the thick protruding portion 259 protrudes from the cover bottom plate 165 of the protecting cover 16.

The opening 161 is disposed between the thick protruding portion 259 and the cover bottom plate 165.

The opening 215 of the protecting cylinder 21 is disposed on the opposed surface portion between the holder 2 and the housing 10, and the open end 108 of the housing 10 is expanded outward so as to define the conduction route 109 of the gas to be measured with the holder 2.

The rest of the construction is the same as that of Embodiment 1.

The oxygen concentration detector of this embodiment has the opening 161 in the cover bottom plate 165 of the protecting cover 16. Therefore, this oxygen concentration detector can prevent moisture from staying between the protecting cover 16 and the protecting cylinder 21 and can discharge the moisture entering the chamber for a gas to be measured 169.

Since the opening 250 described above is formed in the thick protruding portion 259, accidental invasion of the moisture cannot easily occur.

The oxygen concentration detector described above is disposed in the flow of the gas to be measured. Since the thick protruding portion 259 of the protecting cylinder 21 protrudes from the cover bottom plate 165 of the protecting cover 16, the opening 250 is open to the gas flow.

Accordingly, a flow of the gas that flows from the opening 250 to the outside of the oxygen concentration detector occurs, and the quantity of the gas to be measured flowing into and out from the protecting cylinder 21 from the opening 215 can be increased, so that the response of the oxygen concentration detector can be further improved.

the opening 215 of the oxygen concentration detector of this embodiment is disposed in such a manner as to open only to the conduction route 109 disposed between the holder 2 and the housing 10. Therefore, the moisture entering the chamber for a gas to be measured 169 cannot easily enter from the opening 215.

The opening 215 is disposed in the vicinity of the upper portion of the detecting element 12. Therefore, it is spaced apart from the distal end of the detecting element 12 which attains the highest temperature. Even when the moisture enters from the opening 215 and the detecting element 12 is wetted, the wetted portion is the portion at which the temperature is low, and the thermal shock due to wetting is smaller than when the distal end is wetted, so that the occurrence of cracking can be restricted.

This embodiment provides the same function and effect as that of Embodiment 1.

Embodiment 8

This embodiment provides an oxygen concentration detector wherein the opening 250 is formed in the bottom plate 25 of the protecting cylinder 21 and the opening 161 is formed in the cover bottom plate 165 of the protecting cover 16.

The opening 215 of the protecting cylinder 21 is disposed at the opposed portion between the holder 2 and the housing 10, and the open end 108 of the housing 10 is expanded outward so as to define the conduction route 109 of the gas to be measured with, and between, the holder 2.

The rest of the construction is the same as that of Embodiment 1.

The oxygen concentration detector of this embodiment can discharge the moisture entering the chamber 169 for a gas to be measured from the gas inlets 160, through the opening 161 described above. Accordingly, this embodiment can prevent the moisture from staying between the protecting cover 16 and the protecting cylinder 21 and can discharge the moisture entering the chamber 169 for a gas to be measured.

The oxygen concentration detector is disposed inside the flow of the gas to be measured. Therefore, the chamber 169 for a gas to be measured is open to the flow of the gas at its cover bottom plate, and the protecting cylinder 21 is open to the chamber 169 for a gas to be measured at its bottom plate 25. Consequently, a flow of the gas flowing from the opening 250 to the outside of the oxygen concentration detector occurs, and the quantity of the gas to be measured flowing into and out from the protecting cylinder 21 from the opening 215 can be increased, so that the response of the oxygen concentration detector can be further improved.

In the oxygen concentration detector of this embodiment, the opening 215 is so disposed as to open to only the conduction route 109 defined between the holder 2 and the housing 10. For this reason, the moisture entering the chamber 169 for a gas to be measured 169 cannot easily enter from the opening 215.

The opening 215 is disposed in the vicinity of the upper portion of the detecting element 12 and is spaced apart from the distal end of the detecting element 12 which attains the highest temperature. Therefore, even when the moisture enters the opening 215 and the detecting element 12 is wetted, the wetted portion is the one at which the temperature is low and the thermal shock due to wetting is smaller than when the distal end is wetted, so that the occurrence of cracking can be restricted.

This embodiment provides the same function and effect as that of Embodiment 1.

Embodiment 9

Figure 20:
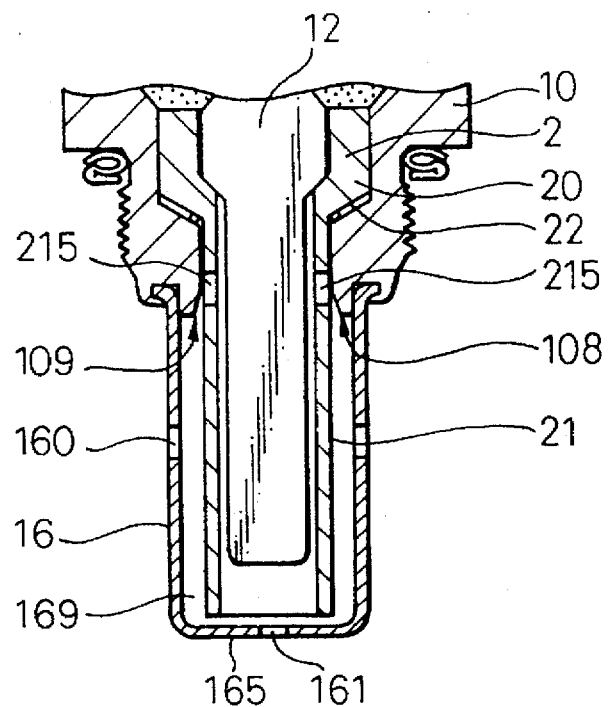
FIG. 20 is a sectional explanatory view of an oxygen concentration detector wherein the lower end of a protecting cylinder is open, according to Embodiment 9 of the present invention.

As shown in FIG. 20, this embodiment provides an oxygen concentration detector wherein the lower end of the protecting cylinder 21 is open, and an opening 161 is formed in the cover bottom plate 165 of the protecting cover 16.

The opening 215 of the protecting cylinder 21 is disposed at the opposed surface portion between the holder 2 and the housing 10, the open end 108 of the housing 10 is expanded outward, and the conduction route 109 of the gas to be measured is formed betweeen the open end 108 and the holder 2.

The rest of the construction is the same as that of Embodiment 1.

The oxygen concentration detector of this embodiment can discharge the moisture entering the chamber 169 for a gas to be measured from the gas inlet ports 160, through the drain port 161. Therefore, it can prevent the moisture from staying between the protecting cover 16 and the protecting cylinder 21 and can discharge the moisture entering the chamber for a gas to be measured 169.

The lower end of the holder 2 is open. Therefore, the oxygen concentration detector can be easily produced.

The oxygen concentration detector is disposed inside the flow of the gas to be measured. Therefore, the chamber 169 for a gas to be measured is open, at its cover bottom plate, to the gas flow and the protecting cylinder 21 is open, at its bottom plate 25, to the chamber 169 for a gas to be measured. Therefore, a flow of the gas flowing from the opening 250 to the outside of the oxygen concentration detector occurs, and the quantity of the gas to be measured flowing into and out from the protecting cylinder 21 from the opening 215 can be increased, so that the response of the oxygen concentration detector can be further improved.

In the oxygen concentration detector of this embodiment, the opening 215 is so disposed as to open to only the conduction route 109 defined between the holder 2 and the housing 10. Therefore, the moisture entering the chamber 169 for a gas to be measured cannot easily enter from the opening 215.

The opening 215 is disposed in the vicinity of the upper portion of the detecting element 12, and is spaced apart from the distal end of the detecting element 12 which attains the highest temperature. Therefore, even when the moisture enters from the opening 215 and the detecting element 12 is wetted, the wetted portion is the one at which the temperature is low, and the thermal impact due to wetting is smaller than when the distal end is wetted, so that the occurrence of cracking can be restricted.

This construction provides the same function and effect as that of Embodiment 1.

Embodiment 10

Figure 21:
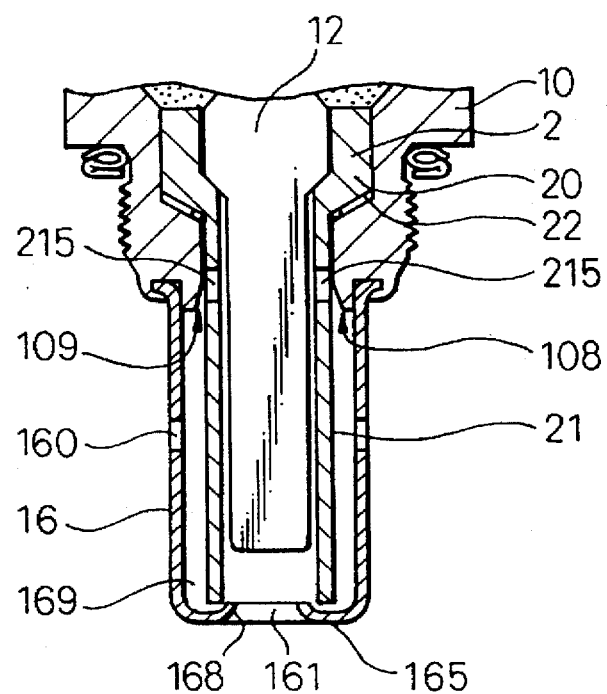
FIG. 21 is a sectional explanatory view of principal portions of an oxygen concentration detector wherein a bent end portion is disposed at an opening of a cover bottom plate, according to Embodiment 10 of the present invention.

As shown in FIG. 21, this embodiment provides an oxygen concentration detector wherein the lower end of the protecting cylinder 21 is open and an opening 161 is defined in the cover bottom plate 165 of the protecting cover 16.

The opening 161 has a bent end portion 168 the end of which is bent towards the open end at the lower end of the protecting cylinder 21.

The opening 215 of the protecting cylinder 21 is disposed at the opposed surface portion between the holder 2 and the housing 10, and the open end 108 of the housing 10 is expanded outward, thereby forming the conduction route 109 of the gas to be measured with, and between, the holder 2.

The rest of the construction is the same as that of Embodiment 1.

The lower end of the holder 2 is open in the oxygen concentration detector of this embodiment and can be easily produced.

The oxygen concentration detector is disposed inside the flow of the gas to be measured. Therefore, the chamber 169 for a gas to be measured is open to the flow of the gas at its cover bottom plate 165, and the protecting cylinder 21 is open to the chamber 169 for a gas to be measured at its bottom plate 25. Therefore, a flow of the gas flowing from the opening 250 to the outside of the oxygen concentration detector occurs, and the quantity of the gas flowing into and out from the protecting cylinder 21 from the opening 215 can be increased, so that the response of the oxygen concentration detector can be further improved.

The bent end portion 168 described above can reduce the clearance between the lower end of the protecting cylinder 21 and the bent open end 168 of the opening 161. Therefore, the moisture flowing from the inlet ports 160 can be trapped with the protecting cylinder 21 and deposition of the moisture to the detecting element 12 can be prevented.

In the oxygen concentration detector of this embodiment, the opening 215 is so disposed as to open only to the conduction route 109 defined between the holder 2 and the housing 10. Therefore, the moisture entering the chamber 169 for a gas to be measured cannot easily enter from the opening 215.

The opening 215 is disposed in the vicinity of the upper portion of the detecting element 12 and is spaced apart from the distal end of the detecting element 12 which attains the highest temperature. Therefore, even when the moisture enters from the opening 215 and the detecting element 12 is wetted, the wetted portion is the portion at which the temperature is low, and the thermal impact due to wetting is lower than when the distal end is wetted, so that the occurrence of cracking can be restricted.

The rest of the construction is the same as that of Embodiment 1.

Embodiment 11

Figure 22:
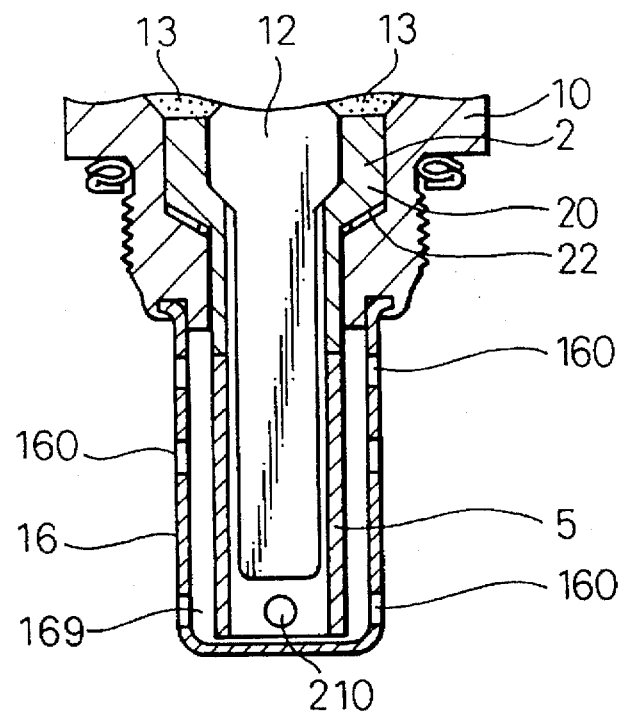
FIG. 22 is a sectional explanatory view of principal portions of an oxygen concentration detector having a protecting cylinder made of a porous insulating ceramic, according to Embodiment 11 of the present invention.
Figure 23:
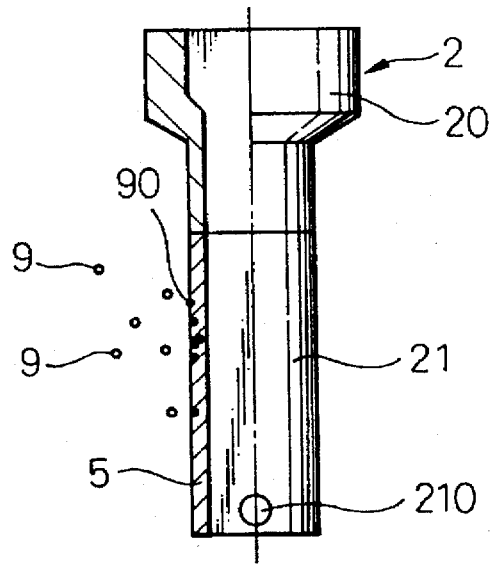
FIG. 23 is an explanatory view of a holder in Embodiment 11.

This embodiment provides an oxygen concentration detector wherein the protecting cylinder is made of a porous body having a high absorption coefficient, as shown in FIGS. 22 and 23.

The oxygen concentration detector of this embodiment has the same construction as that of Embodiment 2, and the protecting cylinder covers the detecting element 12 as a whole. An opening 210 into which the gas to be measured flows is formed on the side surface of the distal end of the protecting cylinder 21 and is so disposed as not to oppose the gas inlets 160 of the protecting cover 16.

The protecting cylinder 5 is made of a porous insulating ceramic different from that of the holder 2. The protecting cylinder 5 is produced separately from the holder 2 and is thereafter integrated with the holder 2 by bonding.

The rest of the construction is the same as that of Embodiment 1.

In the oxygen concentration detector of this embodiment, the protecting cylinder 5 is made of a porous body having a high absorption coefficient. Therefore, when coming into contact with the protecting cylinder 5, the moisture 9 entering the chamber 169 for a gas to be measured is absorbed by the protecting cylinder 5 and is entrapped inside the protecting cylinder 5 (reference numeral 90 in FIG. 23). Accordingly, wetting of the detecting element 12 can be prevented more effectively, and the moisture is prevented more effectively from staying inside the chamber 169 for a gas to be measured.

This embodiment provides the same function and effect as Embodiment 1.

Embodiment 12

Figure 24:
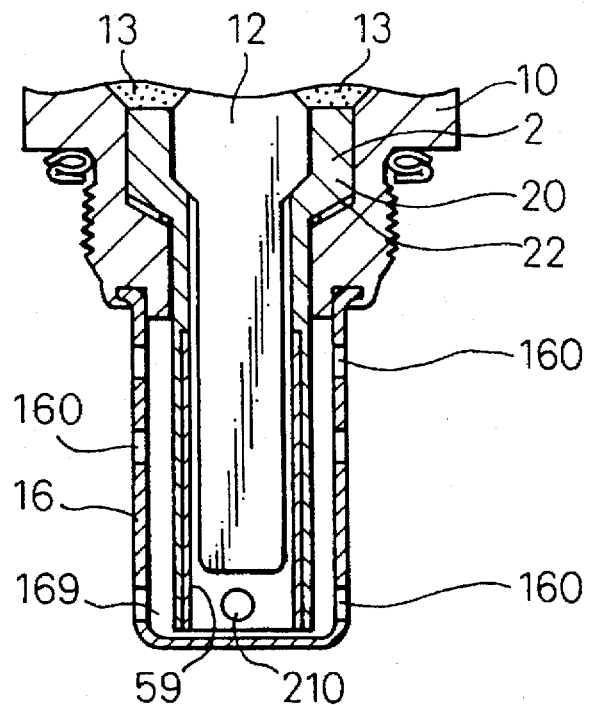
FIG. 24 is a sectional explanatory view of principal portions having a protecting cylinder equipped with a high radiation factor film on the inner surface, according to Embodiment 12 of the present invention.
Figure 25:
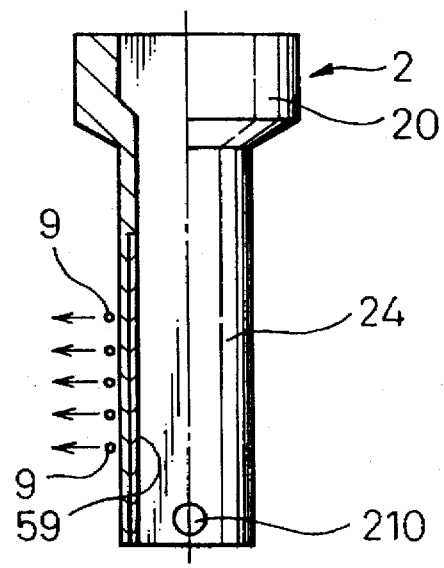
FIG. 25 is an explanatory view of a holder according to Embodiment 12.

This embodiment provides an oxygen concentration detector wherein a high radiation factor film 59 is disposed on the inner surface of the protecting cylinder 21, particularly at the opposed surface portion with the detecting element 12, as shown in FIGS. 24 and 25.

The oxygen concentration detector of this embodiment has the same construction as that of Embodiment 2, and the protecting cylinder 21 covers the detecting element 12 as a whole. An opening 210 in which the gas to be measured flows is disposed on the side surface of the distal end of the protecting cylinder 21, and is so disposed as not to oppose the gas inlet ports 160 of the protecting cover 16.

The high radiation factor film 59 disposed on the inner surface of the protecting cylinder 21 is formed by coating a material having a high radiation factor in the slurry form, and then heating and baking the slurry.

Examples of the materials having a high radiation factor include silicon nitride, aluminum nitride, silicon carbide, titanium oxide, iron oxide, nickel oxide, manganese oxide and cobalt oxide.

The rest of the construction is the same as that of Embodiment 1.

In the oxygen concentration detector of this embodiment, the high radiation factor film 59 is disposed on the inner surface of the protecting cylinder 24. Therefore, the high radiation factor film 59 efficiently absorbs heat of a heater 45 (see FIG. 3) built in the detecting element 12, and the surface temperature of the protecting cylinder 24 rises. Accordingly, the moisture entering the chamber for a gas to be measured comes into contact with the protecting cylinder 24, and is then heated and evaporated as shown in FIG. 25.

In other words, wetting of the detecting element 12 can be more effectively prevented. Further, the moisture is prevented from staying inside the chamber 169 for a gas to be measured.

This embodiment provides the same function and effect as that of Embodiment 1.

Embodiment 13

Figure 26:
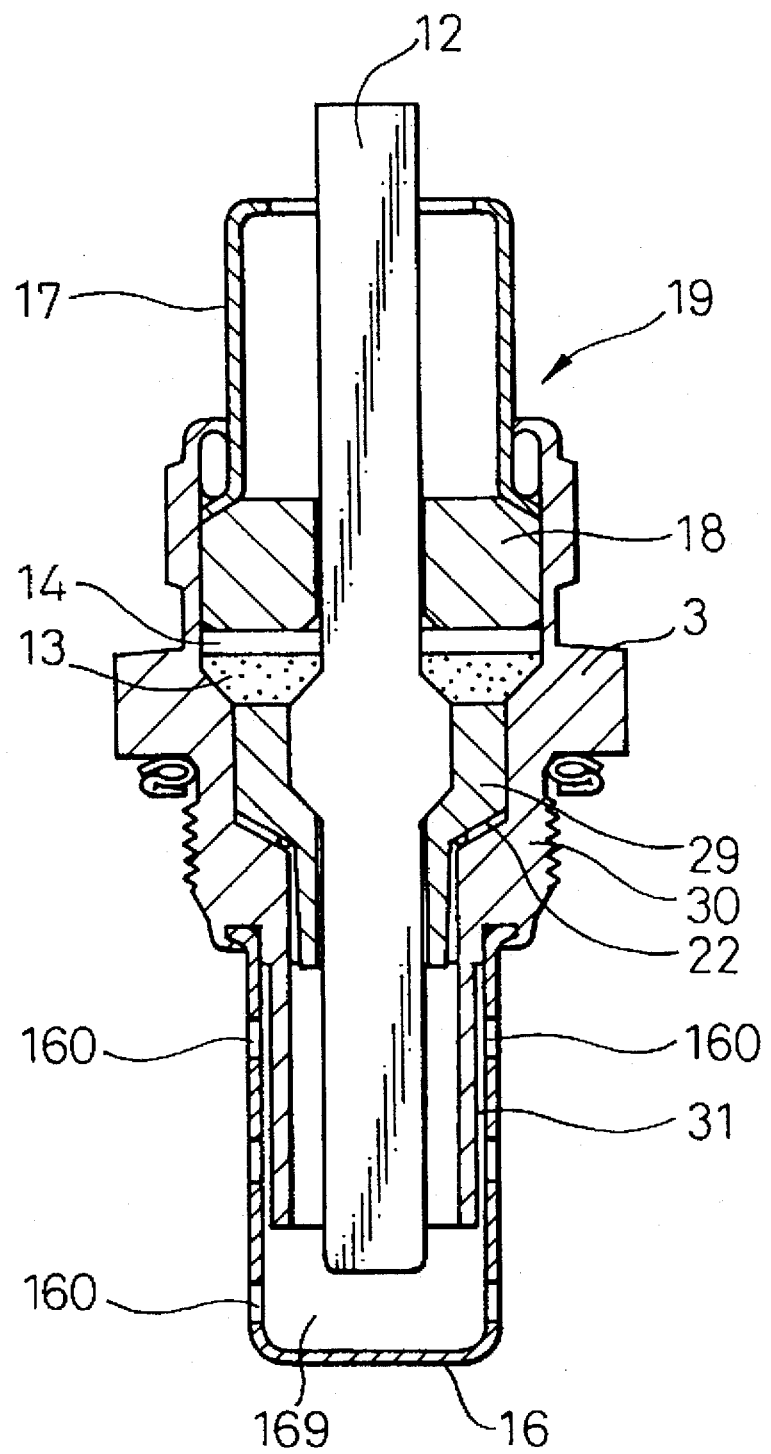
FIG. 26 is a sectional explanatory view of principal portions of an oxygen concentration detector having a protecting cylinder formed by extending a housing, according to Embodiment 13 of the present invention.
Figure 27:
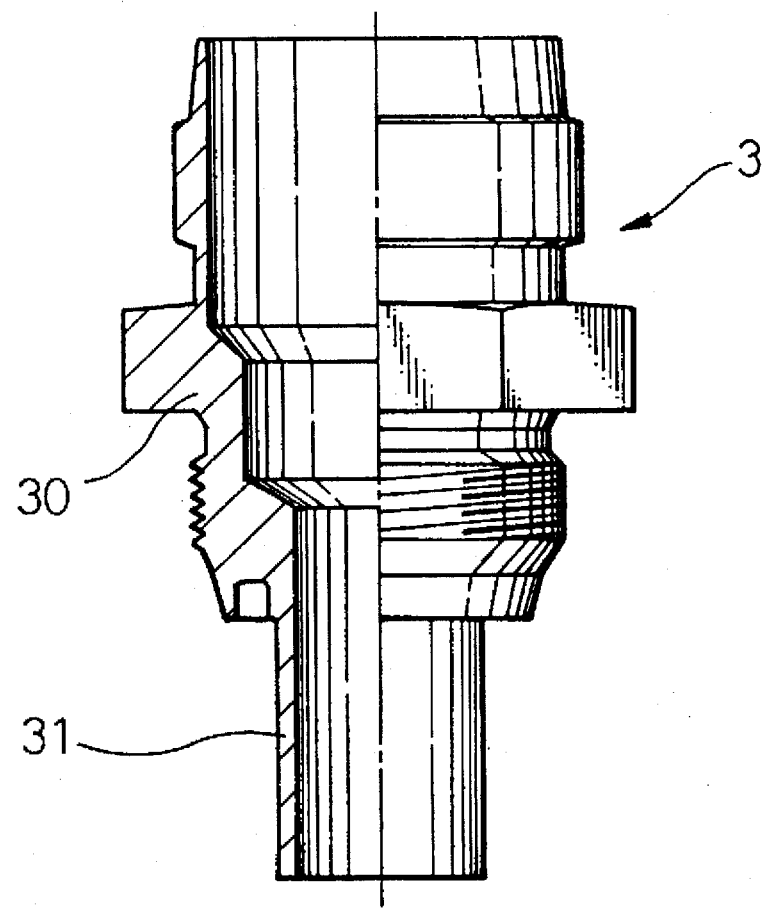
FIG. 27 is an explanatory view of the housing in Embodiment 13.

This embodiment provides an oxygen concentration detector 19 wherein a water-proofing protecting cylinder 31 is formed by extending the housing 3 between the detecting element 12 and the protecting cover 16 as shown in FIGS. 26 and 27.

In other words, the oxygen concentration detector of this embodiment comprises the housing 3, the detecting element 12 loaded into, and disposed inside the housing 3 through the holder 29, and the protecting cover 16 fixed to the housing 3 in such a manner as to cover the outside of the detecting element 12. The protecting cover 16 has a plurality of gas inlet ports 160.

The protecting cylinder 31 formed by extending the housing 30 is disposed between the detecting element 12 and the protecting cover 16. As shown in FIG. 26, the housing 3 comprises the holding portion 30 for holding the holder 29 and the protecting cylinder 31, and both of them are integrally formed. Further, the lower end portion of the protecting cylinder 31 is open.

The housing 3 is made of a stainless steel as a heat-resistant alloy.

In the oxygen concentration detector of this embodiment, the moisture entering from the gas inlet ports 160 of the protecting cover 16 is cut off by the protecting cylinder 31 and cannot easily reach the detecting element 12. Further, the detecting element 12 is difficult to crack.

This embodiment provides the same function and effect as that of Embodiment 1.

Embodiment 14

Figure 28:
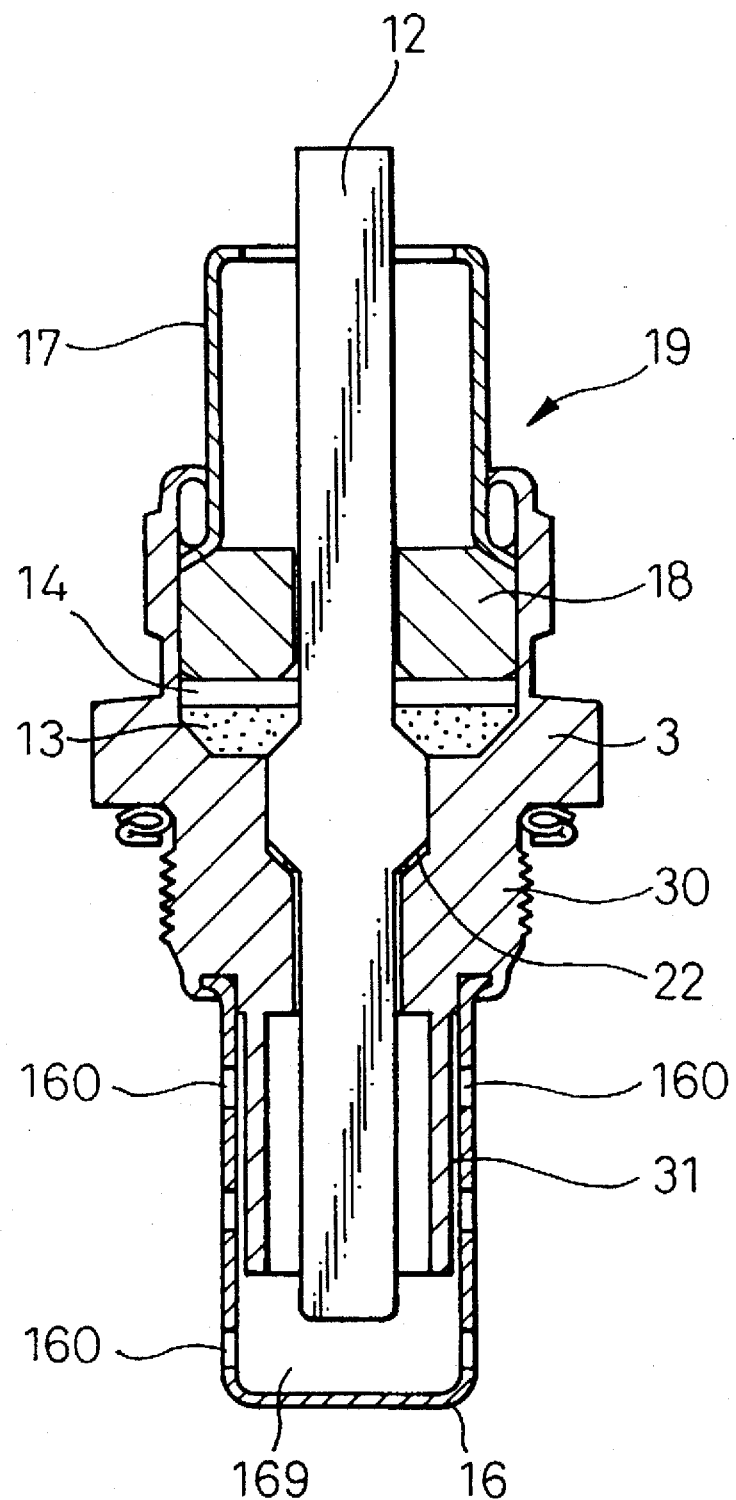
FIG. 28 is a sectional explanatory view of principal portions of an oxygen concentration detector according to Embodiment 14 of the present invention.

In this embodiment, the holder 29 of the oxygen concentration detector shown in Embodiment 12 is omitted as shown in FIG. 28. Because the holder 28 is omitted, this embodiment can reduce the number of necessary components.

This embodiment provides the same function and effect as that of Embodiment 12.

In the above Embodiments, the oxygen concentration detecting element used was a planer type element, but is not limited thereto in the present invention. For example, a cup-shaped oxygen concentration detecting element may be used in the detector of the precent invention, as shown in FIG. 29. In FIG. 29, 12 denotes a cup-shaped oxygen concentration detecting element, 10 a housing, 13 a powder number, 16 a protecting cover, 160 openings in protecting cover 16, 22 and 22' washer packings, 210 an opening in holder 2, 540 a heater, 551 a lead for supplying an electricity to heater 540, 553 a output terminal from the positive electrode of element 12, and 554 a output terminal from the negative electrode of element 12.

We claim:

1. An oxygen concentration detector comprising:
   a) an oxygen concentration detecting element having an elongated shape with first and second ends, said element having a detecting portion and a heater on a side of said first end of said element;
   b) a housing having an outer shape defining a coupling structure, said housing accepting said element inside thereof, the first end of said element protruding from said housing;
   c) an insulating ceramic holder interposed between said housing and said element for holding said element at an intermediate portion of the element, said holder being supported by said housing; and
   d) a protecting cover mounted on said housing and extending toward said first end of said element in the longitudinal direction of said element, said protecting cover being spaced apart from and covering the outside of said element, said protecting cover having gas inlet ports at locations corresponding to said element in the longitudinal direction of said element;
   wherein said holder has between said element and said protecting cover an extended portion thereof spaced apart from and covering the outside of said element, said holder covering at last said gas inlet ports of said protecting cover in the longitudinal direction of said element, said holder thus forming a protecting cylinder for said element.

2. An oxygen concentration detector according to claim 1, wherein said holder has an open end.

3. An oxygen concentration detector according to claim 1 wherein said holder has openings, through which a gas to be measured flows, and said openings are so disposed as not to oppose said gas inlet ports of said protecting cover.

4. An oxygen concentration detector according to claim 1, wherein said protecting cover has a bottom plate.

5. An oxygen concentration detector according to claim 4, wherein said bottom plate of said protecting cylinder has an opening.

6. An oxygen concentration detector according to claim 4, wherein said bottom plate of said protecting cylinder protrudes from the cover bottom plate of said protecting cover, and an opening is formed between said protecting cylinder and said cover bottom plate.

7. An oxygen concentration detector according to claim 4, wherein said bottom plate of said protecting cylinder has a thick protruding portion smaller than the outer diameter of said bottom plate, said thick protruding portion having an opening, the lower end surface of said thick protruding portion exists on the same plane as said cover bottom plate of said protecting cover or protrudes from said cover bottom plate, and an opening is disposed between said thick protruding portion and said cover bottom plate.

8. An oxygen concentration detector according to claim 4, wherein said bottom plate of said protecting cylinder is positioned inside said cover bottom plate of said protecting cover, said bottom plate of said protecting cylinder has an opening, and said cover bottom plate of said protecting cover has an opening.

9. An oxygen concentration detector according to claim 1, wherein said protecting cylinder has openings, through which the gas to be measured passes, closer to said second end of said element than to an end of said housing.

10. An oxygen concentration detector according to claim 1, wherein the lower end portion of said protecting cylinder has an open end, and said protecting cover has a cover bottom plate with an opening.

11. An oxygen concentration detector according to claim 1, wherein said protecting cylinder has an open end, said protecting cover has a cover bottom plate with an opening, and said opening of said cover bottom plate is bent at the end portion thereof in such a manner as to face said open end at the end of said protecting cylinder.

12. An oxygen concentration detector according to claim 1, wherein said detecting element comprises:

a planer solid electrolyte;

a gas-to-be-measured side electrode disposed on a first surface of said planer solid electrolyte;

a reference gas side electrode disposed on a second surface opposite to said first surface of said planer solid electrolyte;

a planer insulator laminated with said planer solid electrolyte, said planer insulator forming a space as a reference gas chamber between said planer solid electrolyte and said planer insulator, said space being closed at a first end portion thereof on the side of said detection side and being open at a second end portion thereof; and a heater formed on said planer insulator on the opposite side to said planer solid electrolyte.

13. An oxygen concentration detector according to claim 12, wherein said detecting element has a flange portion between said first and second ends thereof, and said holder holds said detecting element at said flange portion.

14. An oxygen concentration detector according to claim 1, wherein said detecting element comprises a solid electrolyte having a shape of a cylinder with a closed end, a gas-to-be measured side electrode on an outer surface of said cylinder, a reference gas side electrode on an inner surface of said cylinder, and a heater inside said cylinder.

15. An oxygen concentration detector according to claim 1, wherein said housing has an open end.

16. An oxygen concentration detector comprising:

a) an oxygen concentration detecting element having an elongated shape with first and second ends said element having a detecting portion and a heater on a side of said first end of said element;

b) a housing having an outer shape defining a coupling structure, said housing accepting said element inside thereof, the first end of said element protruding from said housing;

c) an insulating ceramic holder interposed between said housing and said element for holding said element at an intermediate portion of the element, said holder being supported by said housing; and d) a protecting cover mounted on said housing and extending toward said first end of said element in the longitudinal direction of said element said protecting cover being spaced apart from and covering the outside of said element, said protecting cover having gas inlet ports at locations corresponding to said element in the longitudinal direction of said element;

wherein said housing has between said element and said protecting cover an extended portion thereof spaced apart from and covering the outside of said element, said housing covering at least said gas inlet ports of said protecting cover in the longitudinal direction of said element, said housing thus forming a protecting cylinder for said element.

* * * * *